United States Patent [19]

Günzel

[11] Patent Number: 4,627,816

[45] Date of Patent: Dec. 9, 1986

[54] ORTHODONTIC APPARATUS

[76] Inventor: Hans Günzel, Dachauerstr. 65, 8037 Neuesting, Fed. Rep. of Germany

[21] Appl. No.: 735,225

[22] Filed: May 16, 1985

[30] Foreign Application Priority Data

May 23, 1984 [DE] Fed. Rep. of Germany ....... 3419348

[51] Int. Cl.⁴ .............................................. A01C 7/00
[52] U.S. Cl. ......................................... 433/11; 433/13
[58] Field of Search .......................... 433/11, 8, 14, 13

[56] References Cited

U.S. PATENT DOCUMENTS 2,671,964  3/1954  Russell et al. .......................... 433/13
3,477,129  11/1969  Rubin ..................................... 433/11

Primary Examiner—Robert Peshock
Attorney, Agent, or Firm—Richard H. Brink; John J. Balser; Elizabeth O. Slade

[57] ABSTRACT

The wire of an orthodontic appliance is attached at either end to a tooth by means of a lock secured to a band passed around the tooth and having a U-shaped recess into which a retaining spring is set so that when the latch holding the wire is inserted, the ends of the spring catch in notches on the latch thereby affording secure attachment and easy removal and replacement of the wire.

9 Claims, 3 Drawing Figures

ORTHODONTIC APPARATUS

DESCRIPTION

1. Field of the Invention

The invention relates generally to a device for attaching an orthodontic appliance to a tooth and in particular to a lingual lock for securing an orthodontic appliance to a tooth.

2. Background of the Invention

Locks for the attachment of orthodontic arch wires passed along the teeth are known. The arch wire may be anchored to a latch by soldering each end into the openings in the latch. The latch is insertable into a lock which is in turn anchored to a band surrounding a tooth, preferably a molar. In an OREC Newsletter dated April, 1982, a locking arrangement is described wherein the latch is secured against pulling out of the lock by means of the elongated end of the wire being bent into a loop and held in an indentation formed in the lock.

It is known also that the wire itself may be formed into two adjacent loops to be inserted in matching recesses of a lock anchored to the tooth. In this case, the wire is secured against unintentional release by ligating, for example with a retaining wire or ligature.

Various other locks have been disclosed in U.S. Pat. Nos. 1,304,721, 1,362,339, 1,905,877 and 3,477,129. However, these devices require the bending of wires or manipulation and application of multidirectional forces to secure the locking mechanisms.

Accordingly, the object of the invention is to make possible a secure attachment as well as simple removal and quick replacement of the orthodontic appliance.

SUMMARY OF THE INVENTION

In accordance with the invention, the lock is formed from a metal strip which is provided with slits in such a way that after bending to form the lock, recesses are created in which the U-shaped retaining spring can be lodged. The latch bearing the orthodontic appliance is simply inserted in the lock until the retaining spring engages the recesses in the latch, so that the latch is securely held against unintentional release. When the appliance is to be removed, the retaining spring yields upon expulsion or extraction of the latch, and the latch comes free.

BRIEF DESCRIPTION OF THE DRAWINGS

An embodiment of the invention will now be further illustrated by way of example with reference to the drawing, in which.

DETAILED DESCRIPTION OF THE PREFERRED EMBODIMENT

The device consists of a lock 10 and a latch 12 insertable in the lock and held therein.

The two ends of a wire (not shown), passed arcwise along the teeth to be straightened, are each attached to the latch. The anchoring of the ends of the wire by their latches is effected by one lock each, fastened to a metal band passed around a tooth, in particular a molar. The wire passed along the teeth and anchored to a tooth at each end can exert straightening forces on the teeth, or carry fittings by which forces are exerted on the teeth to be straightened. The device according to the invention for anchoring the ends of the wire is preferably applied lingually, i.e., on the side of the teeth towards the tongue, so that the device is concealed. Alternatively, however, the lock may be used to anchor a wire on the outside of the teeth instead.

Figure 1:
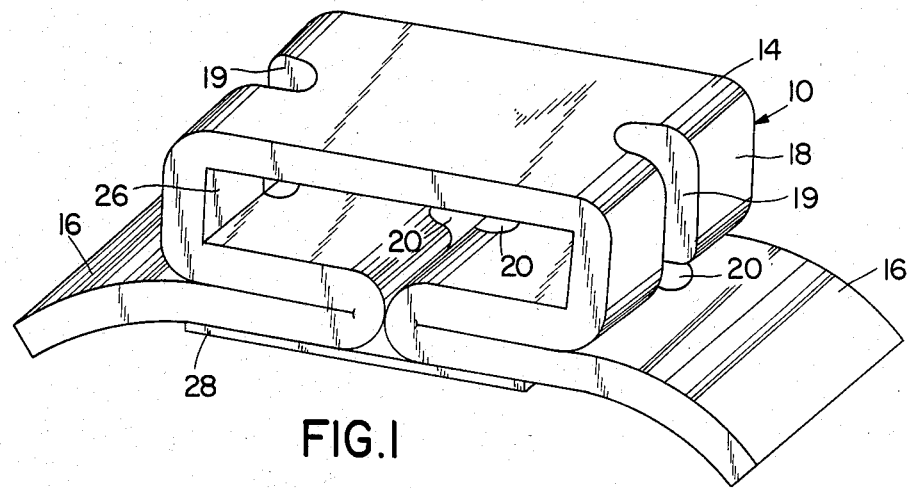
FIG. 1 shows a perspective view of the lock of the the device, without the retaining spring.

The lock 10 is made as shown in FIG. 1 out of a bent strip of metal sheet 14, the insertion passage 15 for the latch 12 being rectangular and arranged to extend in lengthwise direction of the tooth. The two ends 16 of the metal strip are turned back 180° at the midpoint 17 of the lock. The ends 16 serve for attachment of the lock to the band, not shown, passed around the tooth, for example by laser welding.

Figure 2:
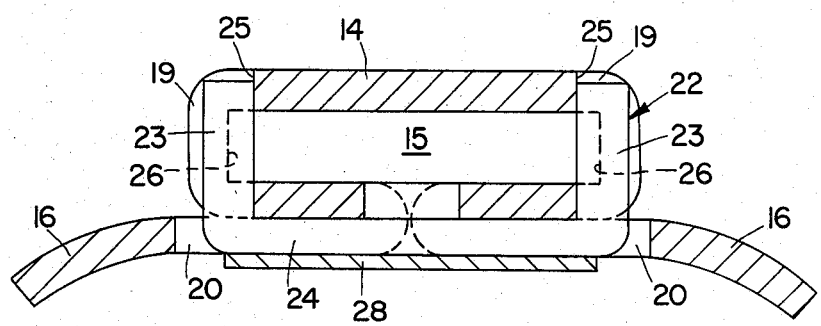
FIG. 2 shows a longitudinal sectional view of the lock with retaining spring; and, FIG. 3 shows a perspective view of the latch of the device.

As shown especially in FIG. 2, the strip of sheet metal is provided with a slit 19 along each side wall 18, and slits 20 are arranged in the turned ends 16 of the strip of sheet metal as well.

Thus in bent condition of the lock 10, the slits 19 and 20 form a U-shaped recess, as seen in lengthwise direction of the lock.

The recess formed by the slits 19 and 20 serves to accommodate a U-shaped retaining spring 22, whose short legs 23 rest in the slits 19 and whose connecting web 24 rests in the aligned slits 20. The length of the slits 19 is so chosen that after the strip of sheet metal has been bent into the shape of the lock as shown, the ends 25 of the slits 19 will lie within the interior 26 of the side walls 18. Thus the legs 23 of the retaining spring protrude laterally into the insertion passage 15. The spring 22 is held in the lock by a cover plate 28 spot-welded to the underside of the ends 16.

Figure 3:
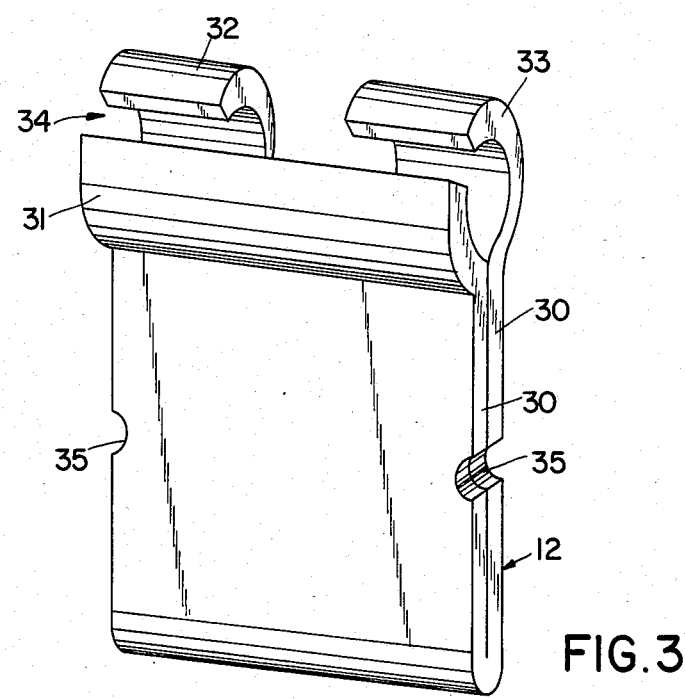

The latch shown in FIG. 3 consists likewise of a metal strip having two legs 30 which are brought into contact with each other by bending the metal strip 180° into the shape shown. The ends 31, 32 and 33 of the legs 30 are bent cylindrically to accommodate a wire (not shown). The ends 31, 32 and 33 are open and form a lengthwise slit 34, so that the ends are easily adjustable to different wire diameters. By means of the divided ends 32, 33 of one of the legs 30, adaptation to the wire diameter is facilitated, since deformation of the ends 32, 33 requires less effort. If desired, however, the two ends can be alike. The wire is secured in the ends by welding and additionally by soldering if required.

On opposed sides of the legs 30, notches 35 are provided. When the latch 12 is inserted in the insertion passage 15 of the lock 10, the legs 23 of the retaining spring 22 will engage the notches 35, holding the latch securely. The latch is removed by lifting or pressing from below, whereupon the spring legs 23 yield, escape from the notches 35, and release the latch.

We claim:

1. Orthodontic arch apparatus comprising
   a lock adapted for attachment to a tooth having a passage therethrough with a least one aperture formed in a side wall of said passage;
   spring means adapted for attachment to said lock, a portion of said spring means extending through said aperture and into said passage;
   a latch adapted for bearing an orthodontic arch wire, said latch being receivable in said passage and having at least one recess adapted for locking engagement with said portion of said spring means.

2. the apparatus of claim 1 wherein said passage extends lengthwise in the direction of the long axis of the tooth.

3. the apparatus of claim 1 wherein two of said apertures are formed in opposite side walls of said passage.

4. the apparatus of claim 3 wherein said two apertures form a U-shaped recess when viewed in the lengthwise direction of said lock.

5. the apparatus of claim 4 wherein said spring means is U-shaped and adapted for locking engagement with said U-shaped recess.

6. the apparatus of claim 1 wherein said passage is polygonal in cross-section.

7. the apparatus of claim 1 wherein said passage is circular in cross-section.

8. the apparatus of claim 1 wherein said passage is elliptical in cross-section.

9. the apparatus of claim 1 wherein said recess is further adapted to provide release of said latch from said lock.

* * * * *